US006004750A

United States Patent [19]
Frank-Kamenetskii et al.

[11] Patent Number: 6,004,750
[45] Date of Patent: *Dec. 21, 1999

[54] NUCLEIC ACID CLAMPS

[75] Inventors: Maxim D. Frank-Kamenetskii, Brookline; Alexei G. Veselkov; Vadim V. Demidov, both of Allston, all of Mass.

[73] Assignee: The Trustees of Boston University, Boston, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/905,567

[22] Filed: Aug. 4, 1997

Related U.S. Application Data

[63] Continuation of application No. 08/546,346, Oct. 20, 1995, abandoned.

[51] Int. Cl.$^6$ .............................. C12Q 1/68; C12P 21/00; C12N 9/00; C07H 21/04
[52] U.S. Cl. .......................... 435/6; 435/69.1; 435/91.1; 435/183; 536/23.1; 536/24.31; 536/24.32
[58] Field of Search .............................. 435/6, 69.1, 91.1, 435/183; 536/23.1, 24.31, 24.32

[56] References Cited

FOREIGN PATENT DOCUMENTS

| | | | |
|---|---|---|---|
| WO92/20703 | 5/1992 | WIPO | ............................ C07K 5/00 |
| WO9220703 | 5/1992 | WIPO | . |
| WO 20702 | 11/1992 | WIPO | . |
| WO 20703 | 11/1992 | WIPO | . |
| WO9312129 | 6/1993 | WIPO | . |
| WO 25706 | 12/1993 | WIPO | . |
| WO 25477 | 11/1994 | WIPO | . |
| WO 01369 | 1/1995 | WIPO | . |
| WO 01370 | 1/1995 | WIPO | . |
| WO 14789 | 6/1995 | WIPO | . |
| WO 16202 | 6/1995 | WIPO | . |

OTHER PUBLICATIONS

Egholm et. al.. Efficient pH–independent sequence–specific DNA binding by pseudoisocytosine–containing bis–PNA. Nuc. Acids Res. vol. 23(2):217–222, Feb. 1995.

Demidov et. al.. Kinetics and mechanism of polyamide ("peptide") nucleic acid binding to duplex DNA. PNAS (USA). vol. 92:2637–2641, Mar. 1995.

Strobel et al., "Single–site enzymatic cleavage of yeast genomic DNA mediated by triple helix formation", *Nature*, vol. 350, Mar. 1991, pp. 172–174.

Hanvey et al., "Antisense and Antigene Properties of Peptide Nucleic Acids", *Science*, vol. 258, Nov. 1992, pp. 1481–1485.

Griffith et al., "Single and Bis Peptide Nucleic Acids as Triplexing Agents: Binding and Stoichiometry", *J. Am. Chem. Soc.* (1995), vol. 117, pp. 831–832.

Nielsen et al., "Sequence–specific transcription arrest by peptide nucleic acid bound to the DNA template strand", *GENE*, (1994) vol. 149, pp. 139–145.

Nielsen et al., "Sequence specific inhibition of DNA restriction enzyme cleavage by PNA", *Nucl. Acid Res.*, (1993) vol. 21, No. 2, pp. 197–200.

Veselkov et al., "PNA as a rare genome–cutter", *Nature*. Jan. 1996, vol. 379, p. 214.

Veselkov et al., "A new class of genome rare cutters" *Nucleic Acids Research*, (1996) vol. 24, No. 13, pp. 2483–2487.

Nielsen, et al., "Peptide Nucleic Acid (PNA). A DNA Mimic with a Peptide Backbone", (1994) Bioconjugate Chemistry, vol. 5, No. 1, pp. 3–7.

Buchardt, et al., "Peptide nucleic acids and their potential applications in biotechnology" (1993), TIBTECH, vol. 11, pp. 384–386.

Cherny, et al., "DNA unwinding upon strand–displacement binding of a thymine–substituted DNA" (1993), Proc. Natl. Acad. Sci. USA, vol. 90, pp. 1667–1670.

Demidov, et al., "Stability of peptide nucleic acids in human serum and cellular extracts", (1994), Biochemical Pharmacology, vol. 48, No. 6, pp. 1310–1313.

Giovannangeli,et al., "Oligonucleotide clamps arrest DNA synthesis on a single–stranded DNA target", (1993), Proc. Natl, Acad. Sci., USA, vol. 90, pp. 10013–10017.

*Primary Examiner*—Nancy Degen
*Assistant Examiner*—William Sandals
*Attorney, Agent, or Firm*—Medlen & Carroll, LLP

[57] ABSTRACT

The invention relates to nucleic acid clamps and methods for using nucleic acid clamps, for example, to inhibit gene expression or cleavage, or to specifically cleave a target nucleic acid. Nucleic acid clamps are molecular devices which can bind nucleic acids with affinity and specificity and have a recognition sequence as small as seven bases. Nucleic acid clamps can be used to modify the effective recognition sequence of restriction endonucleases, reducing the frequency and enhancing the length of the recognition sequence, but without diminishing specificity. The invention also relates to methods for the use of nucleic acid clamps for the treatment of disorders involving abnormal gene expression.

4 Claims, 7 Drawing Sheets

NUCLEIC ACID CLAMPS

This application is a file wrapper continuation of U.S. Ser. No. 08/546,346, filed Oct. 20, 1995, now abandoned.

BACKGROUND OF THE INVENTION

1. Field of the Invention

The present invention relates to nucleic acid clamps that are capable of binding to nucleic acids with high sequence specificity and affinity. The invention also relates to methods of using nucleic acid clamps for the protection and for the selective cleavage of nucleic acids, for the regulation of gene expression and for the treatment of disorders.

2. Description of the Background

Although the structure of the nucleic acid molecule has been known for over 40 years, nucleic acid sequencing has only recently become routine. One of the most important discoveries, which made nucleic acid sequencing practical, was the development of techniques for sequence specific cleavage of nucleic acids. In fact, many molecular biology techniques, including cloning, sequencing, polymorphic loci analysis, restriction profiling, involve nucleic acid cleavage as a required part of the overall protocol.

The most common sequence specific nucleic acid cleavage technique in use today is restriction endonuclease digestion. Restriction endonucleases are one part of a multi-enzyme restriction-modification system (R-M system) used by bacteria to defend itself against foreign nucleic acids. This system protects the organism by digesting foreign nucleic acids found within the cell. Entry of foreign nucleic acid is often the consequence of viral infection or phagocytosis. Restriction endonucleases recognize, bind and cleave a specific sequence, the recognition sequence, of four to eight nucleotide base pairs of double-stranded DNA. Bacterial genomes can be protected from digestion by the specific methylation of recognition sequences, for example, at adenine (A) or cytosine (C) residues by bacterial methylases. Recognition sequences in foreign DNA are generally not methylated and, therefore, can be efficiently cleaved.

The utility of restriction endonucleases to molecular biology has prompted a massive hunt for additional members of this enzyme family. As a result, more than 10,000 prokaryotes have been screened and around 2500 enzymes have been found exhibiting more than 200 distinct recognition sequences (Fasman, ed., *CRC Practical Handbook of Biochemistry and Molecular Biology*, CRC Press, Cleveland Ohio, 1990). Virtually every group of prokaryotes and at least one type of virus contains members that include a restriction endonuclease system.

The restriction-modification system, also referred to as the host-specificity (HS) system, modifies a bacterium's own DNA in a characteristic pattern and degrades or restricts those DNA molecules which lack that distinctive pattern. Degradation of unmodified foreign DNA effectively prevents infection of bacteria by episomes and viruses. Not surprisingly, all restriction-modification systems have at least two features in common, a restriction activity and a modification activity. Modification typically involves methylation of the 6-amino group of adenine residues N4 and C5 of cytosine residues. Sequences comprising the methylated bases are protected from cleavage from restriction endonuclease. As methylase inactivates recognition sites, but not the nuclease, protection of DNA requires methylation of every recognition sequence in a host genome. Some restriction endonucleases are not inhibited by methylation whereas others require methylation for cleavage. Such enzymes protect cells by cleaving foreign DNA which is already methylated.

Restriction activity typically involves at least three types of restriction endonucleases referred to as type I, type II or type III endonucleases. Type I and type III restriction endonucleases contain methylase and nuclease activities in one polypeptide whereas type II restriction endonucleases have no intrinsic associated methylation activity. Methylation activity resides in a distinct polypeptide which generally has the same sequence specificity as the endonuclease. Type II restriction endonucleases recognize a specific and symmetrical cleavage sequence of four to eight nucleotides and generally cut within this recognition sequence. The probability that a given restriction endonuclease will cleave at a site is approximately equal to four to the power of the length of the recognition sequence. Thus, a restriction endonuclease with a recognition site of 4, 5, 6, 7 or 8 base pairs will cleave on the average once every 256, 1024, 4096, 16384 or 65536 base pairs, respectively.

Restriction endonucleases generate double-stranded breaks of a DNA molecule. Typically, this will lead to cell death when repair of the break cannot take place. Unlike type I and type III endonucleases, type II restriction endonuclease is found in virtually every group of prokaryotes. Of the more than 400 type II restriction endonuclease discovered, most have recognition sites of about six base pairs in length. Only a few restriction enzymes have a recognition site of eight base pairs.

DNA methylases can be used to alter the apparent recognition specificity of restriction endonucleases. Unique cleavage specificities may be created in the laboratory by methylating DNA sequences which overlap the recognition site of a restriction endonuclease. These modified sequences are resistant to cleavage by restriction endonucleases. If the recognition sequence of a restriction endonuclease is degenerate, a methylase may be used to modify a subset of the recognition sequence. For example, Hinc II nuclease recognizes the sequences GTCGAC, GTCAAC, GTTGAC and GTTAAC. Taq I methylase methylates the sequence TCGA at the A residue. If DNA is initially methylated with Taq I methylase, those Hinc II recognition sequences containing TCGA, namely GTCGAC, will be resistant to subsequent cleavage by Hinc II.

Another type of methylation modification occurs at the boundaries of the recognition sequence of a restriction endonuclease and a methylase. For example, a Bam HI site (GGATCC) followed by GG or preceded by CC (i.e., GG<u>ATCC</u>GG or CC<u>GGATCC</u>) is a Bam HI site which overlaps a Msp I methylase site (CCGG). Treatment of DNA with Msp I methylase followed by Bam HI endonuclease results in cleavage of all Bam HI sites except <u>GGATCC</u>GG and CC<u>GGATCC</u>. A third method to alter restriction cleavage sites involves the use of restriction endonuclease which only cleaves methylated sites. For example, DNA is first methylated with Taq I methylase that has a recognition site of TCGA. A DNA sequence comprising two or more concatenated Taq I sites (TCGATCGA) will form a Dpn I site (GATC) at the junction. Dpn I is specific only for methylated site and, thus, forms an effective cleavage specificity of two or more Taq sites.

Another method capable of altering the specificity of restriction endonuclease involves the use of PNA, also referred to as peptide nucleic acid or polyamide nucleic acid analog. PNAs are synthetic nucleic acid analogs which can hybridize to form double-stranded structures in a similar fashion as natural nucleic acids. When a PNA strand only contains thymine and cytosine and it can hybridize to homopurine DNA to form a double-strand structure. A second PNA strand can hybridize to this double-strand to form a triple-stranded structure.

Lacking charge and directionality, PNA can bind to DNA in both the sense or antisense orientation. $PNA_2$-DNA or $PNA_2$-RNA has sufficient stability to specifically interfere with DNA recognizing proteins such as methylases, endonucleases, polymerases and transcription factors. PNA may be used to block specific sites on DNA during restriction methylation. After methylation the PNA may be removed and the previously protected sites may be digested with restriction endonuclease. Unprotected sites, methylated by the methylase, will be resistant to attack by nuclease.

Intronic nucleases, while capable of cutting DNA with a reduced frequency are not useful as their choice of cleavage sites are difficult to predict. Some genes of mitochondrial, chloroplast and nuclear DNA and the T-even bacteriophages contain introns that encode endonucleases. The highly degenerate recognition sites for these endonucleases have not been precisely determined. However, the effective cutting frequency is typically one cut per about one million to about 16 million base pairs. The considerable degeneracy of intronic nucleases cleavage sites reduces their general utility for many techniques in molecular biology.

Recent advances in molecular techniques, such as pulsed field electrophoresis and yeast artificial chromosomes, have made the analysis of DNA molecules of up to several million base pairs possible. The ability to physically manipulate large DNA molecules have created new opportunities for molecular biology and placed new demands on restriction endonucleases with a cutting frequency in the range of about one in a million to one in a billion or more.

SUMMARY OF THE INVENTION

The present invention overcomes the problems and disadvantages associated with current strategies and designs and provides nucleic acid clamps and kits containing nucleic acid clamps which are useful in a wide variety of methods for cleaving nucleic acid, for inhibiting nucleic acid-associated interactions and for treating disorders.

One embodiment of the invention is directed to a nucleic acid clamp that can bind to nucleic acids with affinity and sequence specificity. A nucleic acid clamp is a linear polymer comprising two PNA sequences which together can form a triple helix with a target nucleic acid. The two PNA sequences may comprise any PNA residues adapted to hybridize to nucleic acid with specificity such as thymidine, cytosine and pseudoisocytosines or derivatives, analogs of these residues. A bend region which comprises one or more flexible, neutrally charged residues, holds the two PNA sequences together to form the clamp. Residues which can be used in the bend region include, for example, dioxaoctanoic acid or its derivatives or analogs. The stabilizer region comprises one or more positively charged residues, linearly linked, that may be attached to one or both ends or the bend region of the clamp. Positively charged residues may be positively charged amino acids or amino acid derivatives. Examples of positively charged residues include lysine, arginine, ornithine or histidine or their derivatives or analogs.

Another embodiment of the invention is directed to methods for sequence specific cleavage of a target nucleic acid using a nucleic acid clamp and a restriction endonuclease. In one method, a nucleic acid clamp is hybridized to a target nucleic acid. Target nucleic acid is digested with nuclease which cannot cleave sites protected by the nucleic acid clamps. Nuclease may be most any nuclease such as a restriction endonuclease, endonuclease or exonuclease. In this method, the choice of nucleic acid clamps and the nuclease to use may affect the outcome of the digestion. The nucleic acid clamp may, for example, contain a sequence specificity which partially overlaps with the recognition site of a restriction endonuclease. In this case, the nucleic acid clamp will protect a subset of restriction sites from endonuclease cleavage. Alternatively, the nucleases may be an exonuclease which will allow nucleic acid clamps to protect a subpopulation of target nucleic acids from exonuclease digestion. The target nucleic acid may be a natural or synthetic nucleic acid such as, for example, DNA, RNA or PNA.

Another embodiment of the invention is directed to methods of selectively cleaving a target nucleic acid. Target nucleic acid is methylated by restriction methylase following by binding with a nucleic acid clamp. The methylase and the nucleic acid clamp are removed and the target is digested with methylation sensitive restriction endonuclease. By choosing a nucleic acid clamp and a restriction endonuclease with overlapping recognition sequences, a subset of the restriction sites on the target DNA can be selectively methylated. A subset of the restriction sites may be cleaved by the methylation sensitive restriction endonuclease. The choice of restriction endonuclease used will determine whether the methylated or the unmethylated sites are cut as some enzymes only cleave methylated DNA while others only cleave unmethylated DNA. Any enzyme which methylates DNA may be used including dam methylase, dcm methylase, EcoK methylase, CpG methylase, type I modification enzymes, type II modification enzymes and type III modification enzymes.

Another embodiment of the invention is directed to methods for inhibiting an interaction between a nucleic acid binding protein and a target nucleic acid. A nucleic acid clamp is hybridized to a target nucleic acid at a binding site to form a triple helix. The triple helix inhibits interaction between the nucleic acid and protein. Inhibition of binding, for example, destabilizes the nucleic acid and inhibits expression. A number of proteins are involved in gene expression and inhibition of their interaction with nucleic acid may contribute to inhibition of gene expression. Examples of proteins important for gene expression include DNA polymerases, RNA polymerases, reverse transcriptase, ligase, endonucleases, exonucleases, single-stranded DNA binding proteins, double-stranded DNA binding proteins, RNA binding proteins, transcription factors and methylases. Target nucleic acid may be DNA, RNA or PNA, and may be coding, non-coding, controlling or structural nucleic acids.

Another embodiment of the invention is directed to methods for treating a patient with a disorder using a nucleic acid clamp. Treatment involves administration of a therapeutically effective amount of a nucleic acid clamp to a patient with the disorder. The method of administration may be injection, pulmonary absorption, topical application or delayed release. The administered nucleic acid clamp may form a triple helix with one or more target nucleic acids of the patient which may be DNA, RNA or PNA such as a gene, an exon, an intron, a promoter, a splice signal or a structural nucleic acid. Where the target nucleic acid is a promoter sequence, the target may be an enhancer sequence, a distal stimulatory sequence, a proximal stimulatory sequence, a TATA sequence, an initiator sequence, a 3' enhancer sequence, a poly-A addition sequence or a combination of such sequences. A therapeutically effective amount is typically that amount which inhibits expression of a gene. Affects attributed to the nucleic acid clamp may be inhibition of transcriptionl or translation. Disorders which can be treated include neoplastic disorders and infections such as viral disorders.

Another embodiment of the invention is directed to pharmaceutical compositions comprising a nucleic acid clamp and a pharmaceutically acceptable carrier. The pharmaceutical carrier may be selected from alcohols, salts, fatty acids, saccharides, polysaccharides and combinations thereof. Compositions may also contain other agents effective against the disorder.

Another embodiment of the invention is directed to kits for the selective cleavage of nucleic acids. Kits may comprise a nucleic acid clamp, a restriction methylase and a restriction enzyme with overlapping recognition specificities. The kit may be designed to allow a user to cleave a nucleic acid sequence at a specific sequence.

Other embodiments and advantages of the invention are set forth, in part, in the description which follows and, in part, will be obvious from this description and may be learned from practice of the invention.

DESCRIPTION OF THE INVENTION

The present invention relates to nucleic acid clamps which bind to nucleic acids with high sequence specificity and affinity. The invention also relates to methods for using nucleic acid clamps for the selective cleavage of nucleic acids and for sequence-specific inhibition of protein-nucleic acid interactions and also to kits which comprise these clamps. Nucleic acid clamps of the invention are also useful in the regulation of gene expression and in the treatment of disorders related to gene expression.

Nucleic acid clamps are molecular devices designed to bind with both high affinity, high binding strength or avidity, and high specificity to a target sequence. The nucleic acid clamp may be used to protect a subset of restriction cleavage sites in a target from cleavage. Used in conjunction with a restriction endonuclease, a nucleic acid clamp converts a frequent cutting restriction enzyme into a rare cutter. By choosing a nucleic acid clamp with the proper sequence specificity, a restriction endonuclease may be converted by this method.

Nucleic acid clamps have a number of surprising properties which make them useful for binding to a target nucleic acid. Typically, agents which demonstrate sequence-specific binding have a diminished ability to discriminate matches from mismatches (affinity or tenacity) and, conversely, agents with a high affinity have low specificity. The nucleic acid clamp has high specificity and affinity. Furthermore, the nucleic acid clamp can be easily separated from target. An additional advantage of the nucleic acid clamp is that within the number of useful bases (C and T analogs) a clamp of nearly any sequence and any length can be synthesized. For example, an 8 bp clamp may be of any one of 256 sequences while a 12 bp clamp may of any one of about 4000 sequences. The large number of possible sequences, and the even larger number of nucleic acid clamps restriction endonucleases combinations allows for an enormous possibility of recognition sequence to exist.

The nucleic acid clamp is partly comprised of peptide nucleic acids (PNA) and as such, may be referred to as a peptide nucleic acid clamp. Peptide nucleic acids, unlike natural nucleic acids, are constructed upon an achiral backbone which is without substantial charge at neutral pH. These properties allow substantial freedom in the binding of nucleic acid clamps. While nucleic acids generally hybridize to each other in an antiparallel formation, nucleic acid clamps can hybridize in parallel, antiparallel and multimeric (e.g. triplex) configurations.

Preferably, PNA is a synthetic analog of nucleic acids which may have the general structure of:

The typical structure of PNA comprise a polymer with a backbone (A, B) attached to evenly spaced nucleobases, optionally, by linkers (L). A and B are components of the backbone and may be the same or different. Typical backbones are polyamides which may be modified by thiolation such as, for example, forming a polythioamide, a polysulphinamide or a polysulphonamide, or another modified polyamide. The nucleobases may comprise natural nucleobases or synthetic nucleobases. Natural nucleobases comprise purines such as adenine, guanine, inosine or pyrimidines such as thymine, uridine, or cytosine. Synthetic nucleobase which mimics purines and pyrimidines such as 5-propynylthymine, 3-deazauracil, 6 thioguanine, purine-6 (1H)-thione and pyrazolo[4,3-d]pyrimidines may also be used.

Linkers may comprise a wide variety of groups including, for example, the groups —$CH_2CO$—, —$CONR^3$—, —$NR^3CONR^3$—, —$CR^1R^2CO$—, —$CR^1R^2CS$—, —$CR^1R^2CSe$—, —$CR^1R^2CNHR^3$—, —$CR^1R^2C=CH_2$— and $CR_1R_2C=C(CH_3)_2$, propanoyl, butanoyl, pentanoyl, ($C_2$–$C_6$) alkylene or ($C_2$–$C_6$) alkylene substituted with $R^1R^2$, may also serve as linkers. $R^1$ and $R^2$ may be independently selected from hydrogen, ($C_1$–$C_4$) alkyl. Examples of ($C_1$–$C_4$) alkyls include hydroxy, alkoxy or alkylthio-substituted, hydroxy, alkoxy, alkylthio, amino and halogen. Attachment of the linker to the nucleobase, and also the backbone, may be through single or multiple bonds.

Preferably, the backbone is a polymer of alternating AB subunits which may be based on, for example, polymers of 2-aminoethylglycine. A may be a nitrogen atom, in which case the backbone may be achiral. Alternatively, A may be an $R^3N^+$ wherein $R^3$ may be a hydrogen, ($C_1$–$C_4$) alkyl, hydroxy, alkoxy, alkylthio or an amino group. B may be an —$CR^6R^7$—, —$CHR^6CHR^7$—, or —$CR^6R7CH_2$—, wherein $R^6$ and $R^7$ may be independently select from hydrogen, ($C_2$–$C_6$) alkyl, aryl, aralkyl, heteroaryl, hydroxy, ($C_1$–$C_6$) alkoxy, ($C_1$–$C_6$) alkylthio, $NR^3R^4$, $SR^5$, pyrrolyl, furyl, thienyl, imidazolyl, pyridyl, pyrimidinyl or indolyl. $R^6$ and $R^7$ may also be selected together to form an alicyclic system such as 1,2-cyclobutanediyl, 1,2-cyclopentanediyl or 1,2-cyclohexanediyl.

Nucleic acid clamps display unusual resistance to natural nucleases. Most natural nucleases are adapted to recognize and cleave the ribose based backbone of nucleic acids. The backbone of the nucleic acid clamps, while sufficiently similar to natural nucleic acids for efficient hybridization, is also sufficiently dissimilar to be resistant to nuclease. This property contributes to a longer half-life and extends the utility of the nucleic acid clamp in vitro and in vivo therapy.

Another embodiment of the invention is directed to a method for using a nucleic acid clamp to inhibit protein-nucleic acid interactions. Many biological processes and laboratory procedures rely on proper protein nucleic acid interactions. Examples of these processes include cell growth, differentiation, metabolism, gene regulation, viral growth, restriction digest, sequencing and polymerase chain reaction. The methods of the invention allow the complete inhibition or the alteration of specificity of these processes. By inhibition or by alteration, nucleic acid clamps expand the number of techniques available to the laboratory worker and expand the procedures available for the treatment of disorders.

Another embodiment of the invention is directed to a method for using nucleic acid clamps to create new restriction sites with reduced cutting frequency. Most restriction endonucleases recognize sites that are from four to six and in a few cases eight base pairs in size and, thus, cleave most genomic DNA into a very large number of fragments. Physical mapping of large genomes for the creation of genomic libraries or for genomic sequencing requires methods which cleave nucleic acids with a reduced frequency. A method for reduced frequency cleavage of nucleic acids is useful in many branches of molecular biology such as genome mapping, genome sequencing and forensic science. In this method, the nucleic acid clamp is used to protect a subset of restriction endonuclease sites from methylation. These protected sites are subsequently cleaved by methylation sensitive endonuclease. Thus, reduced frequency cleavage using nucleic acid clamps may be accomplished by protecting sites from endonuclease or from methylase. A nucleic acid clamp may be specific for and hybridize to a sequence of 4, 6, 8, 10, 12 or more bases in length.

A part of the nucleic acid clamp recognition site may overlap the restriction and methylation site of a restriction modification system such that when the nucleic acid clamp is bound, the nucleic acid is resistant to methylases and endonucleases. For example, the nucleic acid clamp may be designed to bind with high affinity and specificity to an eight base target DNA, which overlaps by two bases with a four base restriction endonuclease and methylase site. Target nucleic acids are first treated with a nucleic acid clamp, followed by methylation by site specific methylase. After methylation, methylase is inactivated and removed along with the nucleic acid clamp. Targets are next cleaved with restriction endonuclease leaving only the unmethylated sites, those formerly protected by a nucleic acid clamp, susceptible to cleavage. A four base restriction endonuclease and an eight base nucleic acid clamp will cut nucleic acids with an effective recognition site of 10 bases.

Another embodiment of the invention is directed to nucleic acid clamps which can form triplexes with both DNA, RNA and, under appropriate conditions well-known to those of ordinary skill in the art, PNA. DNA and RNA are two similar chemical polymers comprising subunits referred to as nucleotides. A nucleotide comprises a purine or pyrimidine base linked through its nitrogens to a ribose backbone. The five carbon cyclic sugar backbone is ribose for RNA and deoxyribose for DNA. This backbone has chirality and charge at neutral pH. Because of these characteristics, triple helices formed with natural nucleic acids are not as stable as double-stranded nucleic acids and require protons and an acidic pH for formation. Unlike triplexes formed with natural nucleic acids, triple helices comprising a nucleic acid analog such as PNA are typically more stable because PNA lack chirality and charge.

PNA is a synthetic oligonucleotide mimic in which the common DNA or RNA bases are attached via a linker to an N-(2-aminoethyl)glycine backbone. In PNA, the chiral backbone of natural nucleic acids is replaced with an achiral backbone having the same interbase distances as natural DNA and RNA. The achiral backbone has sufficient rigidity and flexibility to allow PNA to hybridize with DNA, RNA and other PNAs. The lack of charge and chirality allows DNA•PNA, RNA•PNA and PNA•PNA duplexes to be formed in both the parallel and antiparallel orientation. Of the two orientations for duplexes, the antiparallel orientation is slightly more thermodynamically favored. The lack of charge and the ability to form parallel duplexes also allows PNA to form triple helices by itself, or with DNA, RNA, PNA or combinations of DNA, RNA and PNA. In PNA triplex formation, two homopyrimidine PNAS may bind a single-stranded target nucleic acid and the target may be DNA or RNA. If the target nucleic acid is double-stranded, one of the original double strands is displaced by this reaction to produce a P-loop structure comprising a $PNA_2$/DNA triplex and a displaced strand.

Surprisingly, PNA exhibits two apparently contradictory features: highly sequence specific and very strong binding. This combination causes $PNA_2$/DNA triplexes to have remarkable stability. The stability of triplexes comprising PNA, which simulates the behavior of proteins specifically interacting with nucleic acids, stems from two-stage kinetics of the triplex formation. At the first searching stage, a highly unstable but sequence-specific duplex is formed between PNA and the complementary DNA or RNA strand. On the second stage of stable triplex formation, the second PNA molecule hybridizes to the duplex and locks into a triplex. In this $PNA_2$DNA triplex, one polypyrimidine PNA strand forms a Watson-Crick base pairing with the polypurine nucleic acid while the other polypyrimidine PNA strand associates by Hoogsteen base paring with the purines in the duplex region without disruption the conventional Watson-Crick pairs.

Resultant triple helixes are completely resistant to methylation or restriction endonuclease cleavage. Nucleic acid clamps, comprising two PNA molecules connected with a flexible linker is more efficient in targeting nucleic acids than monomeric PNAs. Additional stabilization of the P-loop at neutral pH can be achieved by replacing cytosines in one half of bis-PNA with pseudoisocytosines.

To achieve sequence specificity and affinity, a triple helix region of 12 bases is preferred for optimal stability. Nucleic acid clamps, by juxtaposing a flexible bend region and positively charged stabilizers residues, are able to form triple helixes with as few as about five, six, seven or about eight bases or more. This surprising ability allows for considerable flexibility in the use of nucleic acid clamps.

PNA which binds to 12 bp of nucleic acids will have a binding frequency of about $(¼^{12})$ or one site per 4.3 billion bases. On the average, this represents less than one cut per human genome. This cleavage frequency is sometimes too small. An advantage of the nucleic acid clamp is that it may have a binding site of 47 to 412, representing from less than one to 180,000 cuts per human genome. This range of cutting frequencies is useful in many procedures. Furthermore, unlike other methods of cleaving nucleic acids such as partial digestion, the nucleic acid clamp cleaves with sequence specificity. Thus, the resultant fragments are predictable in both size and sequence, and reproducible.

Another embodiment of the invention is directed to methods for using nucleic acid clamps to digest target nucleic acids in a sequence specific manner. Nucleic acid clamps may have a wide sequence specificity. Preferably, sequence specificities are between about 5 to about 20 bases, more preferably from about 6 to about 15 bases, and even more preferably from about 8 to about 12 bases. A nucleic acid clamp, adapted to recognize a specific sequence, is added to the target nucleic acids. The recognition sequence of the nucleic acid clamp comprises both the cleavage recognition sequence of a restriction endonuclease as well as flanking sequences. The subset of restriction sites with the flanking sequence recognized by the nucleic acid clamp remain undigested by the restriction endonuclease while the remaining sites are cleaved.

Another embodiment of the invention is directed to a method of cleaving a target nucleic acid by treating the target with a nucleic acid clamp, a methylase and a restriction endonuclease. Nucleic acid clamps and methylases may be used to alter the apparent recognition specificity of restriction endonuclease. The altered specificity is sequence specific, user definable and increases the utility and the list of cleavage sequences which can be utilized. A nucleic acid clamp, adapted to hybridize to a subset of the recognition site of a restriction methylase, is added to a target nucleic acid. After the nucleic acid clamp is hybridized, target nucleic acid is methylated with restriction methylase. Both the methylase and the nucleic acid clamp are removed leaving a target nucleic acid with two classes of restriction endonuclease sites that are methylated and unmethylated. The addition of a methylation sensitive restriction endonuclease will selectively cleave only one class of sites.

The choice of which class of sites to cleave is made by the restriction enzymes used. Some restriction enzymes, such as Eco RI, cleave unmethylated sites while other restriction enzymes such as Dpn I are specific for methylated sites. By adding a restriction enzyme that cleaves specifically at methylated sites or at unmethylated sites, cleavage of a subset of sites can be performed.

Figure 4:
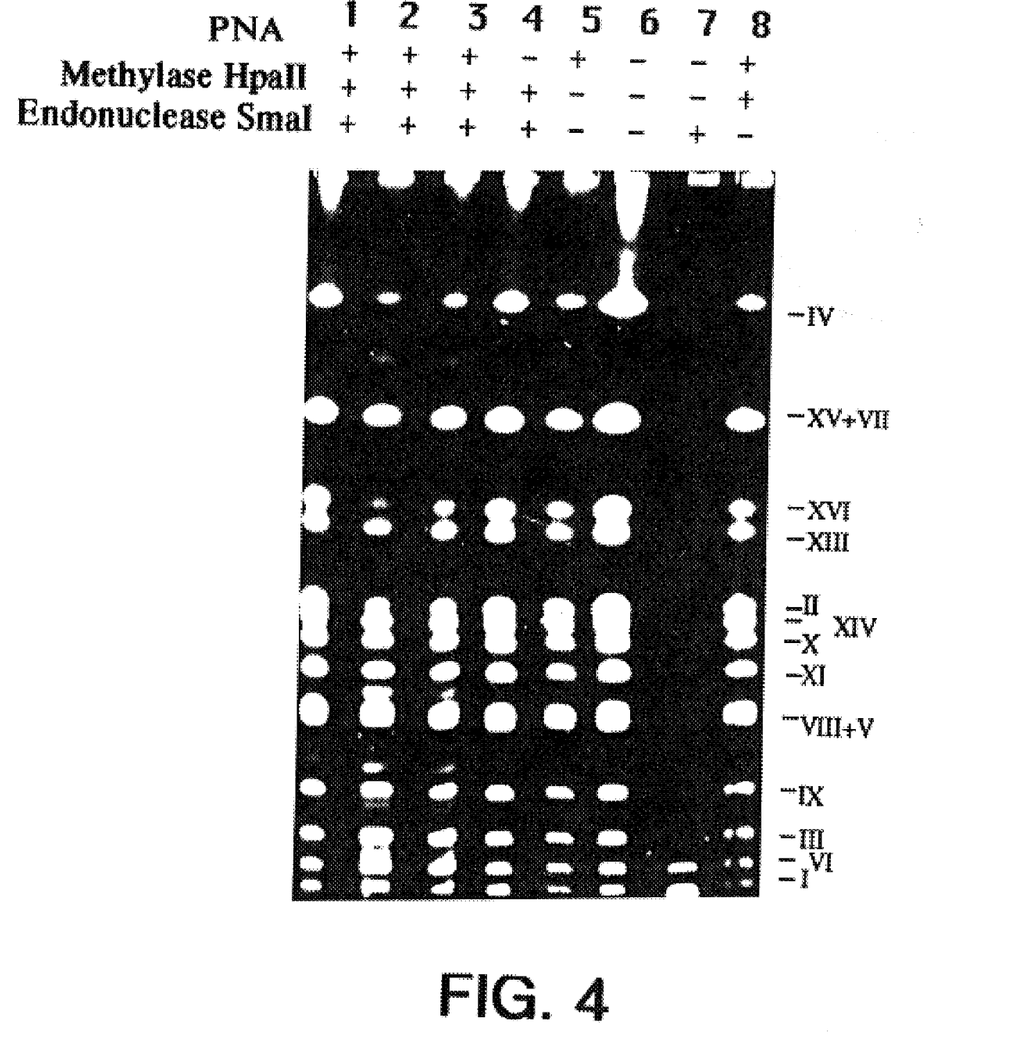
FIG. 4 Nucleic acid clamp alters cleavage specificity of Hpa II methylase/Sma I endonuclease treatment.

A nucleic acid clamp, in combination with an appropriate pair of methylation-restriction enzymes may form a new class of genomic rare cutters. Although pyrimidine sequences of PNAs can be used, pyrimidine 8-mers provide with a large pool of $2^8=256$ different sequences. Combining this pool with a large pool of known methylation/restriction pairs of enzymes, can create a large variety of rare cutters. The most frequent are expected to produce, theoretically, fragments in the Mbp range (because the recognition site corresponds to eight base pairs recognized by PNA overlapping with 2 bp of 4-bp long restriction site, so it consists of 10 bp). In practice, cutting may occur more often if the number of restriction sites is much larger than expected, as is apparently the case for Hpa II restriction site (CCGG) in yeast genome (FIG. 4). Increasing the length of PNA and/or using restriction endonucleases with larger recognition sites allows for the creation of unique rare cutters in a genome of most any size. Thus, this method allows for the rapid and specific alteration of the sequence specificity of a restriction endonuclease.

One advantage of such methods is that the nucleic acid clamps may be generated by conventional automated peptide synthesis and oligonucleotide synthesis techniques. Automatic synthesis allows for the rapid creation of a nucleic acid clamp adapted for a particular recognition sequence. Multiple nucleic clamps with different specificity may be synthesized in rapid succession by reprogramming the automated synthesizers. In addition to altering the specificity of a restriction endonuclease, this method allows for the adjustment of cleavage specificity as well.

Another embodiment of the invention is directed to methods for the use of nucleic acid clamps in forensics such as in identification. Forensic techniques using endonucleases rely primarily on loci with a few polymorphic restriction sites. Loci with too many or too few polymorphic sites are generally problematic. As the size of the loci studied can generally be extended significantly in both the 5' and the 3' side, and site frequency increases linearly with size, too many restriction sites are generally more of a problem than too few. In addition to restriction site polymorphism, useful loci are limited to those with well defined banding patterns. If a restriction enzyme causes too many bands to develop, results can be difficult to interpret. Thus, frequent cutting restriction endonucleases are frequently not used in forensic identification. Nucleic acid clamps may be used to reduce the number of restriction sites at a locus, allowing the use of frequent cutting restriction endonucleases. The number of loci and the number of restriction endonuclease useful for forensic detection is increased with the use of nucleic acid clamps.

Another embodiment of the invention is directed to a method for the use of nucleic acid clamps to inactivate ribonuclear proteins. Abnormal expression of ribonuclear proteins has been implicated in many disorders. For example, cancer and aging have been associated with abnormal expression of telomerase, a ribonuclear protein. Nucleic acid clamps may be designed to specifically form triple helixes with the ribonucleic acid component of telomerase. Assembled triple helical regions prevent the assembly of the ribonuclear protein and, thereby, inhibit telemerase function and assist in the treatment of telomerase-related diseases.

Another embodiment of the invention is directed to a method for the use of nucleic acid clamps in polymerase chain reaction (PCR). One type of obstacles to PCR are competing side reactions such as the amplification of non-target sequences in background nucleic acid and primer oligomerization. If the sequence of the background band is known, a nucleic acid clamp may be used to inhibit amplification of the background band to enhance the detection of the signal. For example, primer dimers, artifact bands in PCR with a sequence corresponding to the sum of the two primers, are often a problem with PCR. To specifically inhibit primer dimers, the PCR primers may be designed such that the primer dimer sequence comprises a nucleic acid clamp recognition site at the junction of the two primer sequences. In the absence of primer dimers, the nucleic acid clamp does not bind and no inhibition occurs. If a primer dimer is formed, the nucleic acid clamp quickly binds to it and inhibits further rounds of PCR amplification and reducing the background signal.

Another embodiment of the invention is directed to a method for the use of nucleic acid clamps to treat disorders. Many disorders in humans such as neoplastic diseases, are due to the inopportune expression of genes. The relationship between abnormal gene expression and disease is well-known in the case of certain neoplastic disorders. Many naturally occurring tumors are found to express or overexpress an oncogene and neoplasms can be induced in vitro and in vivo by the over expression of oncogenes. Nucleic acid clamps may be used to treat disorders by inhibiting the transcription of specific genes.

For example, a specific nucleic acid clamp can be administered to a patient to inhibit gene expression. The nucleic acid clamp may bind to a target nucleic acid to prevent gene expression by, for example, binding sequences which comprise origins of DNA replication, a transcription promoter, a transcription enhancer, a transcription initiator, a coding sequence, splicing signals, a poly-A signal, a protein binding site, a translation start signal or a translation termination signal. In this capacity, nucleic acid clamps may act as promoter clamps, translation clamps, translation clamps, gene clamps, replication clamps, expression clamps or binding site clamps.

In addition to inhibition of gene expression, nucleic acid clamps may also be used to enhance gene expression by, for example, binding to and inhibiting the expression of an inhibitor. The suppressor may be a transcriptional inhibitor, a translational inhibitor or a posttranscriptional modification inhibitor. By preventing expression or action of the inhibitor, the nucleic acid clamps enhance the expression of genes previously suppressed.

Therapeutic agents comprising nucleic acid clamps may be more stable than agents which comprise natural nucleic acids. Compared to nucleic acid clamps, natural nucleic acids, are subjected to cleavage by a variety of natural nucleases. Thus therapeutic agents comprising a nucleic acid clamp may have longer stability in vivo, a longer shelf life and less demanding storage conditions.

For example, a nucleic acid clamp designed to bind to sequences comprising or surrounding elements such as promoters, enhancers, initiators or terminators, may prevent transcription factors from binding the same sites thus preventing transcription. Nucleic acid clamps designed to bind to sequences important to splicing such as RNA splice sites or to the nucleic acids of small nuclear ribonucleoproteins may disrupt splicing and RNA processing ultimately disrupting and gene expression. For example, nucleic acid clamps which bind sequences important for translation such as Kozak sequence prevent translation.

Another embodiment of the invention is directed to compositions comprising nucleic acid clamps plus a pharmaceutically acceptable carrier such as water, saline, alcohol, polyethylene glycol, oil, polysaccharides, salts, glycerol, stabilizers, buffers, antioxidants, emulsifiers and combinations thereof. The function of the carrier is to provide a suitable medium for introduction of the construct in or on the patient's body. When compositions are used internally, carriers of saline, buffer and salts maybe useful. When used externally, carriers such as water, oils and alcohols may be useful. Compositions may further comprise other ingredients such as antioxidants to prevent oxidation of constructs, anti-bacterial or anti-viral agents to reduce contamination, or other chemotherapeutic agents to treat the disorder. Compositions may also be combined with other agents that are effective or suspected to be effective against the disorder.

Another embodiment of the invention is directed to a method for treating or preventing a disorder in a patient comprising the steps of administering a nucleic acid clamp, specific to a nucleic acid sequence related to the disorder, to the patient. The disorder to be treated may be any disorder which involves the overexpression of a nucleic acid sequence such as a gene. For example, in a neoplastic disorder, a nucleic acid clamp may be specific for genes and mRNA encoding oncoproteins such as Myc, Gli, Mas, Met, Neu, Ras, Trk, Onc, Thy, Bcl, Tcl, Evi, Int, Mlvi, Erb, Src, Raf, Jun, Fos, Pim, Glv, Gin, Fis, Lck, Dsi, Fim, Ahi, Mis and Spi.

Sequences to be targeted for treatment may be determined by the symptoms displayed. For example, Burkitt lymphoma patients may benefit from inhibition of the myc gene. In a similar way, patients infected with the human immunodeficiency virus may benefit from the inhibition of HIV specific genes such as reverse transcriptase.

Disorders in which constructs and compositions may be used for therapeutic or prophylactic purposes include infections, neoplasias and genetic defects and deficiencies. Neoplasias treatable in this manner include leukemias, lymphomas, sarcomas, carcinomas, neural cell tumors, squamous cell carcinomas, germ cell tumors, metastases, undifferentiated tumors, seminomas, melanomas, neuroblastomas, mixed cell tumors, neoplasias caused by infectious agents and other malignancies. Treatable infections include infections caused by bacteria, viruses and parasites, and also fungal infections such as yeast and deep fungal infections which are difficult to treat conventionally. Prophylactic uses of the nucleic acid clamps include placing the clamp in the point of entry of the virus. For example, nucleic acid clamps may be incorporated into lotions applied to the surface of humans. Viruses and infectious particles which come into contact with the nucleic acid clamps may be neutralized. As another example, blood and blood products may be treated with the nucleic acid clamp to reduce the risk of transmitting infectious diseases.

Treatments may be administered topically to treat or prevent diseases and infections on the exterior of the patient, or administered parenterally, sublingually, rectally or enterally, to treat or prevent systemic disorders. Patients which may be treated with these methods include animals and preferably humans.

The following experiments are offered to illustrate embodiments of the invention and should not be viewed as limiting the scope of the invention.

EXAMPLES

Example 1

Nucleic Acid Clamps to Alter Endonuclease Cleavage Specificity

The nucleic acid clamp PNA-669 comprises bis-PNA containing pseudoisocytosines with a sequence of, H-Lys$_2$-TJJJJTTJ-(egl)$_3$CTTCCCCT-LysNH$_2$. This clamp carries four positive charges that additionally stabilize the PNA$_2$/DNA complexes. This PNA has high specificity and affinity for a unique 8 bp binding site on λ-DNA. This nucleic acid clamp binding site overlaps with one of the 121 Taq I sites on λ-DNA located at position 27,981:

```
    PNA target site
5' TCCCCTTC GA 3'        (SEQ ID NO:1)
3' AGGGGAAG CT 5'        (SEQ ID NO:2)
       Taq I site
```

Figure 1:
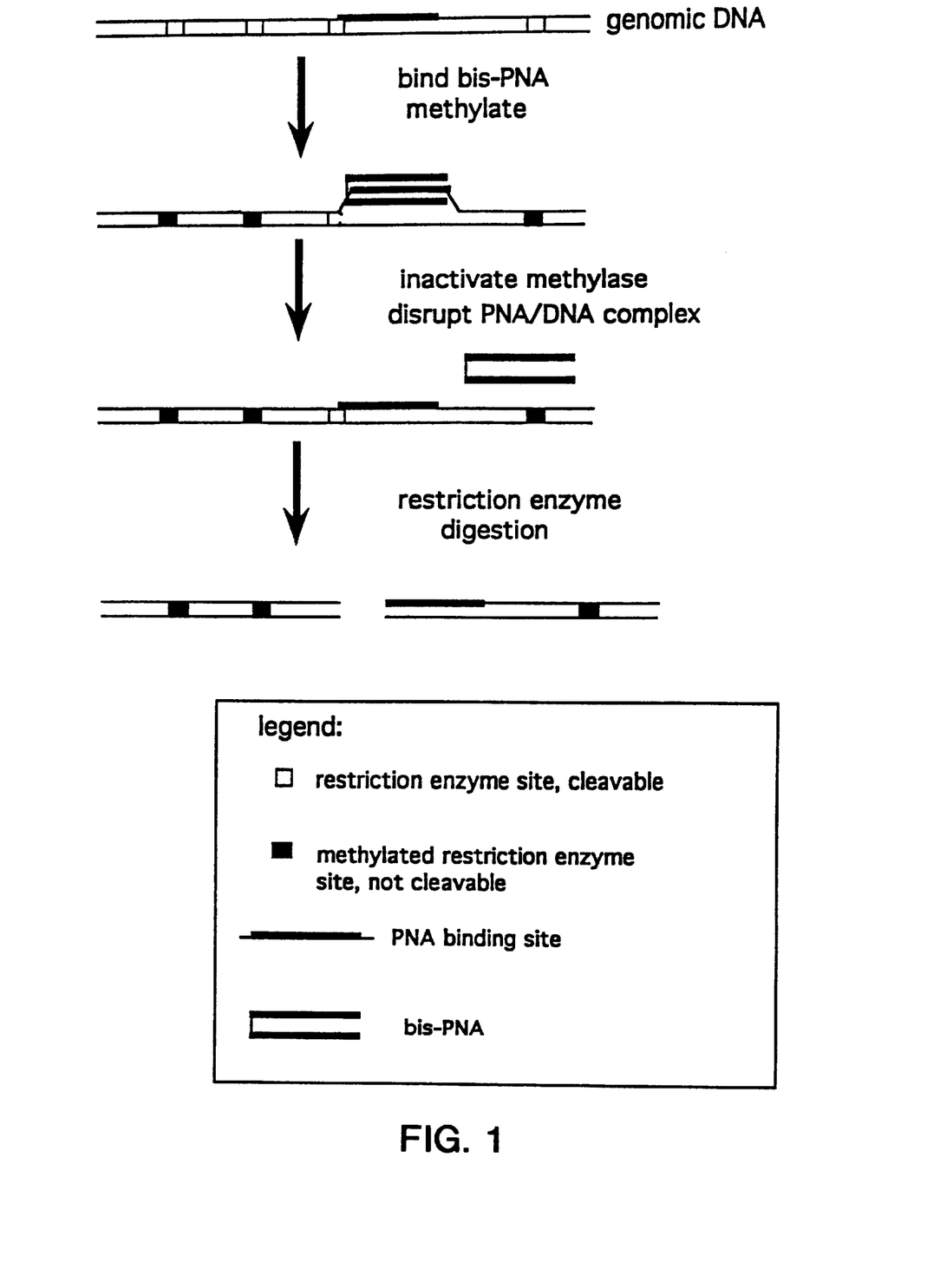
FIG. 1 Schematic demonstration of the use of a nucleic acid clamp to alter enzyme specificity.

The mechanism of nucleic acid digestion is shown in FIG. 1. A nucleic acid clamp is applied to a target nucleic acid comprising multiple restriction endonuclease sites. The nucleic acid clamp is adapted to hybridize to only one of the sites. Methylase is applied to the target resulting in methylation of all sites except the ones protected by the nucleic clamp. Upon the removal of the nucleic acid clamp and the methylase, only the previously protected site is left unmethylated. Thus, the addition of restriction endonuclease cleaves the nucleic acid only at the previously protected site. Use of PNA 669 and Taq I endonuclease effectively cleaved a site of 8 base pairs (Table 1: TCCCCTTCGA)(SEQ ID NO:1).

Example 2

Cleavage of λ-DNA After Treatment with Nucleic Acid Clamp

To determine the ability of the nucleic acid clamp to inhibit protein DNA interaction, λ-DNA was treated with PNA-669 which comprises a sequence of H-Lys$_2$-TJJJJTTJ-(eg1)$_3$-CTTCCCCT-LysNH$_2$. Briefly, γDNA, embedded in a 7 μl 0.65% a low-melting agarose plug was equilibrated by shaking at 37° C. in a buffer comprising, 20 mM MES, 2 mM EDTA, pH 6.3 (37° C.), 10 mM NaCl. The embedded DNA was transferred to 100 μl of the same buffer with PNA-669 (H-Lys$_2$-TJJJJTTJ-(eg1)$_3$-CTTCCCCT-LysNH$_2$) for 5.5 hours at 37° C.

After formation of triple helixes, the nucleic acid PNA complex was methylated by equilibration in buffer containing 25 mM sodium citrate, 10 mM NaCl and 5 mM β-mercaptoethanol, pH 7.2 (37° C.) and incubated overnight with one unit of Cvi B III methylase and 100 μg/ml bovine serum albumin at 4° C. in 15 μl of the same buffer. 0.15 μl of 32 mM S-adenosylmethionine was added and methylation was performed for an additional 1.5 hours at 37° C. The reaction was stopped and the PNA-DNA complex was dissociated by incubation for 50 minutes at 58° C. in 200 μl, 50 mM Tris-HCl, 500 mM NaCl, 10 mM EDTA, pH 8.9 and 1% SDS.

The samples were equilibrated in 1× reaction buffer (20 mM Tris-acetate, 10 mM magnesium acetate, 50 mM potassium acetate, 1 mM DTT, pH 7.9 at 25° C.) and digested with 1 unit αTaq I restriction endonuclease was performed in 35 μl of the same buffer and 100 μg/ml bovine serum albumin for 2 hours at 55° C. The reaction was stopped by incubating for 10 minutes with 200 μl of 50 mM EDTA, pH 7.5. Then the samples were equilibrated in TE pH 7.5 heated at 68° C. for 6 minutes and loaded onto a 1% agarose gel. The pulse-field gel electrophoresis (PFGE) was run on CHEF MAPPER system (Bio-Rad).

Figure 2:
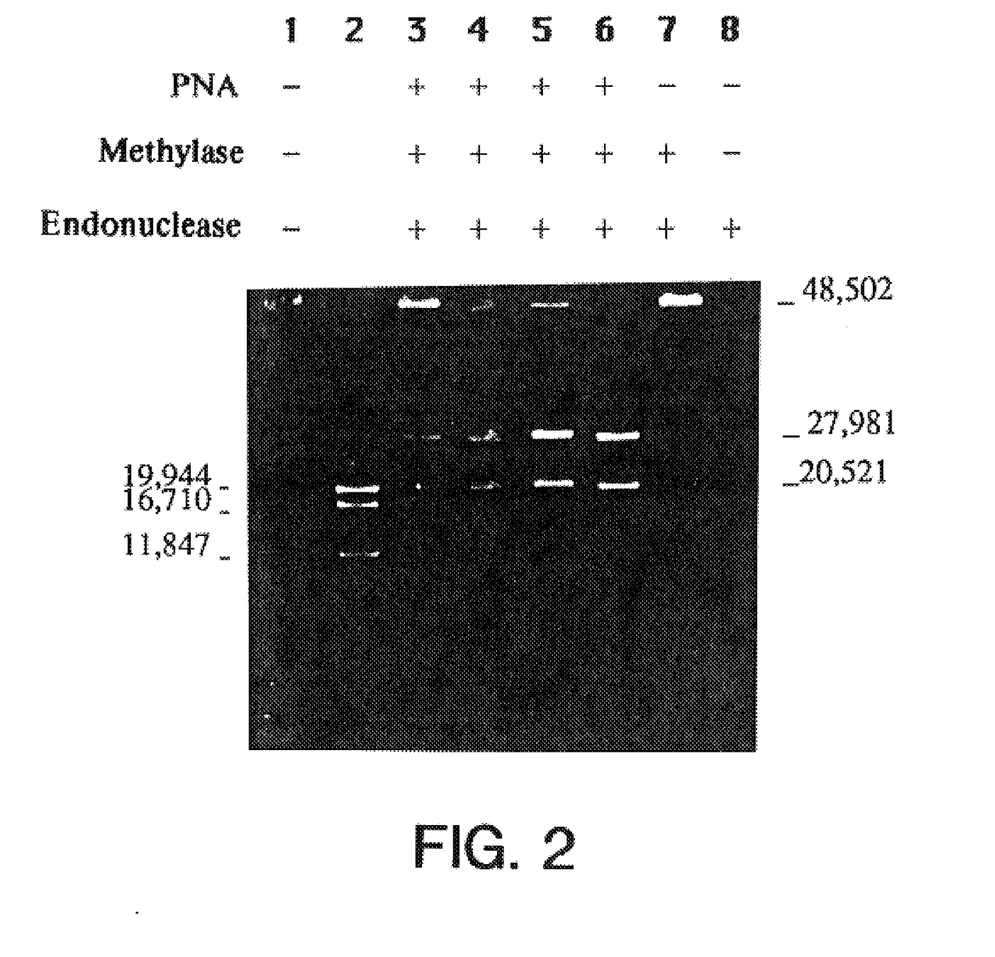
FIG. 2 Restriction endonuclease digestion of a nucleic acid treated with varying amounts of a nucleic acid clamp and a methylase.

The result of the gel electrophoresis analysis is shown in FIG. 2. Lane 1 and 2 represent analysis of untreated λ-DNA and molecular weight markers (Eag I digested λ-DNA) respectively. Lanes 3, 4, 5 and 6 contain γ-DNA treated with 0.015, 0.018, 0.02 and 0.025 optical units of PNA-669, respectively. Lane 7 and lane 8 contains completely methylated or untreated λ-DNA which was subsequently treated with Taq I endonuclease and used as positive and negative controls, respectively.

Example 3

Digestion of Yeast Genome After Nucleic Acid Clamp Treatment

Figure 3:
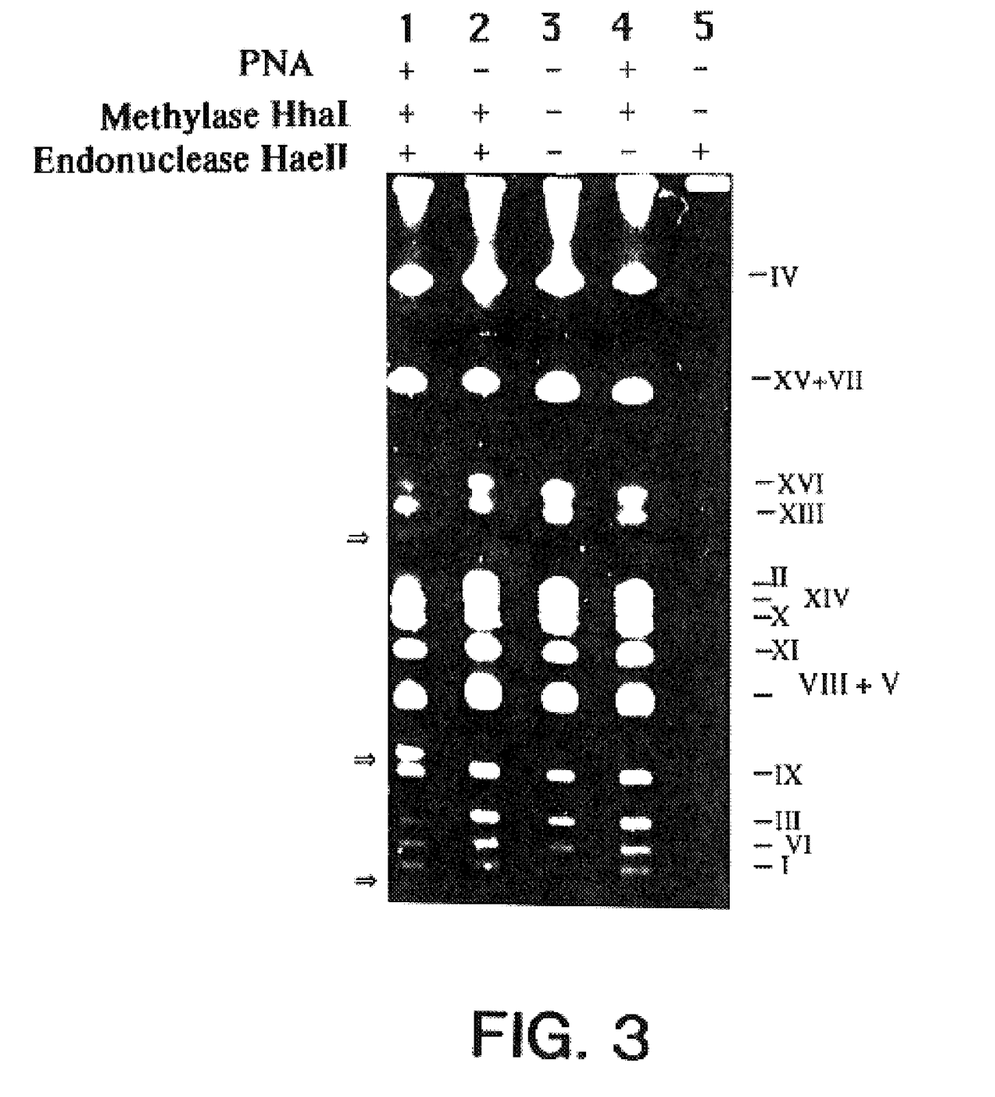
FIG. 3 Nucleic acid clamp alters cleavage specificity of Hha I methylase/Hae II endonuclease treatment.

A yeast genome was used to determine the effectiveness of nucleic acid clamp treatment on large DNA fragments. Yeast DNA from PSY316 strain in a 0.65% low-melting agarose plug of 7 μl was equilibrated in 20 mM MES, 2 mM EDTA, pH 6.3 (37° C.), 10 mM NaCl, and incubated with shaking in 300 μl of the same buffer with 0.03 o.u. of PNA-669 for 10 hours at 37° C. Samples were equilibrated in buffer containing 25 mM sodium citrate and 5 mM β-mercaptoethanol, pH 7.0 (37° C.), and were incubated overnight with 15 units of methylase Hha I at 4° C. in 16 μl of the same buffer and 100 μg/ml bovine serum albumin. Then 0.2 μl of 32 mM S-adenosylmethionine was added and methylation was performed at 37° C. for 2.5 hours. The reaction was stopped and the PNA-DNA complex was dissociated by incubation for 50 minutes at 58° C. in 200 μl, 50 mM Tris-HCl, 500 mM NaCl, 10 mM EDTA, pH 8.9 and 1% SDS. Samples were equilibrated in 1× reaction buffer (20 mM Tris-acetate, 10 mM magnesium acetate, 50 mM potassium acetate, 1 mM DTT, pH 7.9 at 25° C.) and digestion with 4 units Hae II restriction endonuclease was performed in 25 μl of the same buffer and 100 μg/ml bovine serum albumin for 4 hours at 37° C. The reaction was stopped by incubating for 20 minutes in 200 μl of 50 mM EDTA, pH 8.7. Samples were equilibrated in TE, pH 7.5, and loaded onto a 1% agarose gel. The pulse-field gel electrophoresis was run on CHEF MAPPER system (Bio-Rad). Results are shown in FIG. 3. Lane 1 contains yeast DNA digested with Hae II after treatment with nucleic acid clamp and Hha I methylase. A new band, the result of specific digestion appears between chromosomes VIII+ V and chromosome IX. This band is not present if the DNA was not treated (lane 3), or if PNA (lane 2) or endonuclease was omitted (lane 4). The addition of restriction endonuclease alone results in complete digestion of the nucleic acid (lane 5).

The ability of two separate nucleic acid clamps to modify restriction endonuclease cleave was tested, analyzed by PGFE and the results are shown in FIG. 4. The target was yeast genome DNA (strain PSY316) and the nucleic acid clamps applied was PNA-669 (H-Lys$_2$-TJJJJTTJ-(eg1)$_3$-CTTCCCCT-LysNH$_2$) and PNA-668 (H-Lys$_2$-TTTJTTJJ-(eg1)$_3$-CCTTCTTT-LysNH$_2$). Nucleic acid clamps were used at a concentration of 0.055 o.u and the procedure were performed using Hpa II methylase/Sma I endonuclease pair of enzymes. Briefly, PNA-668 was incubated with DNA for 5 hours, with Hpa II methylase enzyme for 4 hours and with 4 units of the Sma I enzyme for 4 hours at 25° C. Lanes 1 represents the results of the proposed strategy in case of PNA-668. Lanes 2 and 3 shows the same results in case of PNA-669. For lane 2, 8 units of methylase were used, for lanes 1 and 3, 12 units were used. Other lanes present various control experiments: lane 4 gives results of methylation-digestion without PNA; lane 5 present results of incubation with PNA, but without enzymes; lane 6 gives intact genome; lane 7 present digestion of the yeast genome with the Sma I enzyme; lane 8 gives results for PNA-669 and methylation, but without restriction endonuclease treatment.

Figure 5:
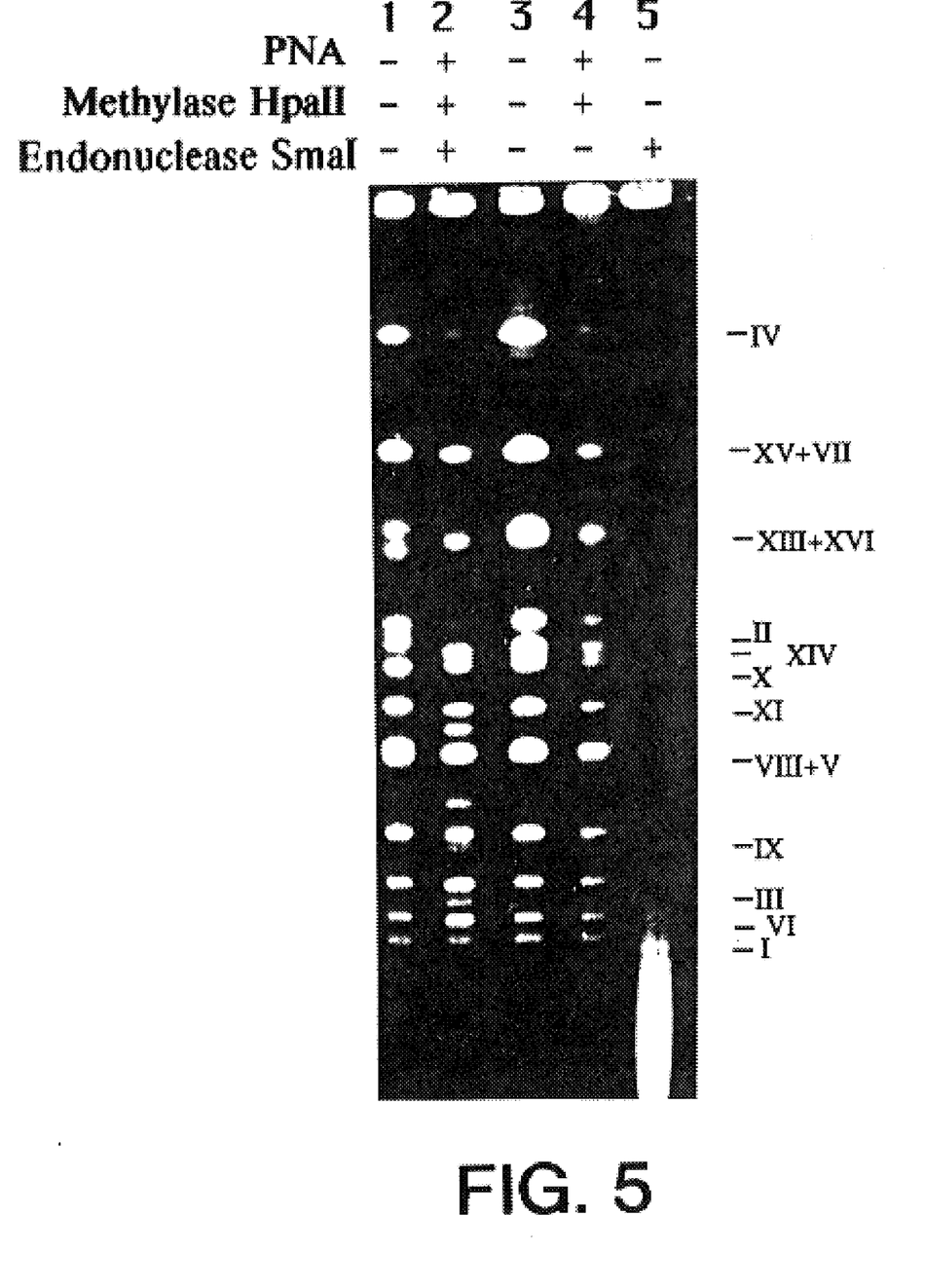
FIG. 5 Analysis of restriction fragment size following nucleic acid clamp/Hpa II methylase/Sma I endonuclease treatment.

The experiment was repeated with nucleic acid derived from another yeast strain (BP1) and nucleic acid clamp PNA-669. Results are shown in FIG. 5. Lanes 1: untreated PSY316 genome. Lanes 2–5 correspond to the BP1 strain.

Example 4

Nucleic Acid Clamp Effectiveness

Figure 6:
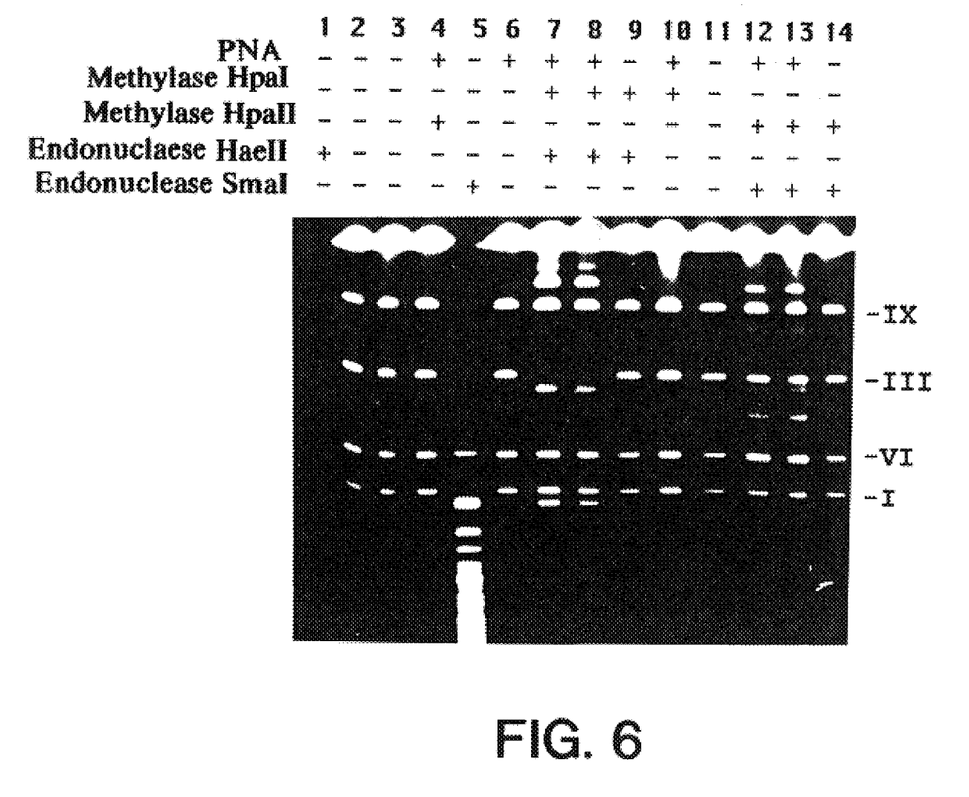
FIG. 6 A test of the ability of two separate nucleic acid clamps to interfere with nucleic acid protein interaction.

To determine the effectiveness of the nucleic acid clamp in the inhibition of methylase, nucleic acids were treated by nucleic acid clamp 669 and enzymes and examined by pulsed field gel electrophoresis. The electrophoresis conditions were set for the analysis of nucleic acid less than 500 kbps in size. Results of the analysis are shown in FIG. 6.

Lane 1 and 5 represent yeast DNA showing complete digestion with Hae II or Sma I restriction endonuclease, respectively. Lane 2 comprise untreated yeast DNA and Lane 3, and lane 11 comprise yeast DNA incubated in buffer, but otherwise not treated with nucleic acid clamps or enzymes. This shows that the starting material and the buffers are devoid of nucleases. Yeast DNA treated with a nucleic acid clamp and either Hha I methylase or Hpa II methylase are analyzed in lanes 4 and 10, respectively, indicating that the nucleic acid clamp and the methylases do not comprise nuclease activity. lane 6 contains yeast DNA treated with a nucleic acid clamp only. Lanes 7 comprises yeast DNA treated with a nucleic acid clamp, 20 units of methylase Hha I and Hae II restriction endonuclease. Lane 8 is identical to lane 7 except that 25 units of methylase were used. Methylation protection, and subsequent selective endonuclease cleavage are shown in lanes 7 and 8. Lane 9 is identical to lane 7 except no nucleic clamp was used leading to complete methylation and complete inhibition of restriction endonuclease. The same series of experiment using a different set of enzymes are shown in lanes 12, 13 and 14. Lane 12 comprises yeast DNA treated with a nucleic acid clamp, 10 units of methylase Hpa II and Sma I restriction endonuclease. Lane 8 is identical to lane 7 except that 15 units of methylase were used. Lane 9 is identical to lane 7 except no nucleic clamp was used.

Example 5

Figure 7:
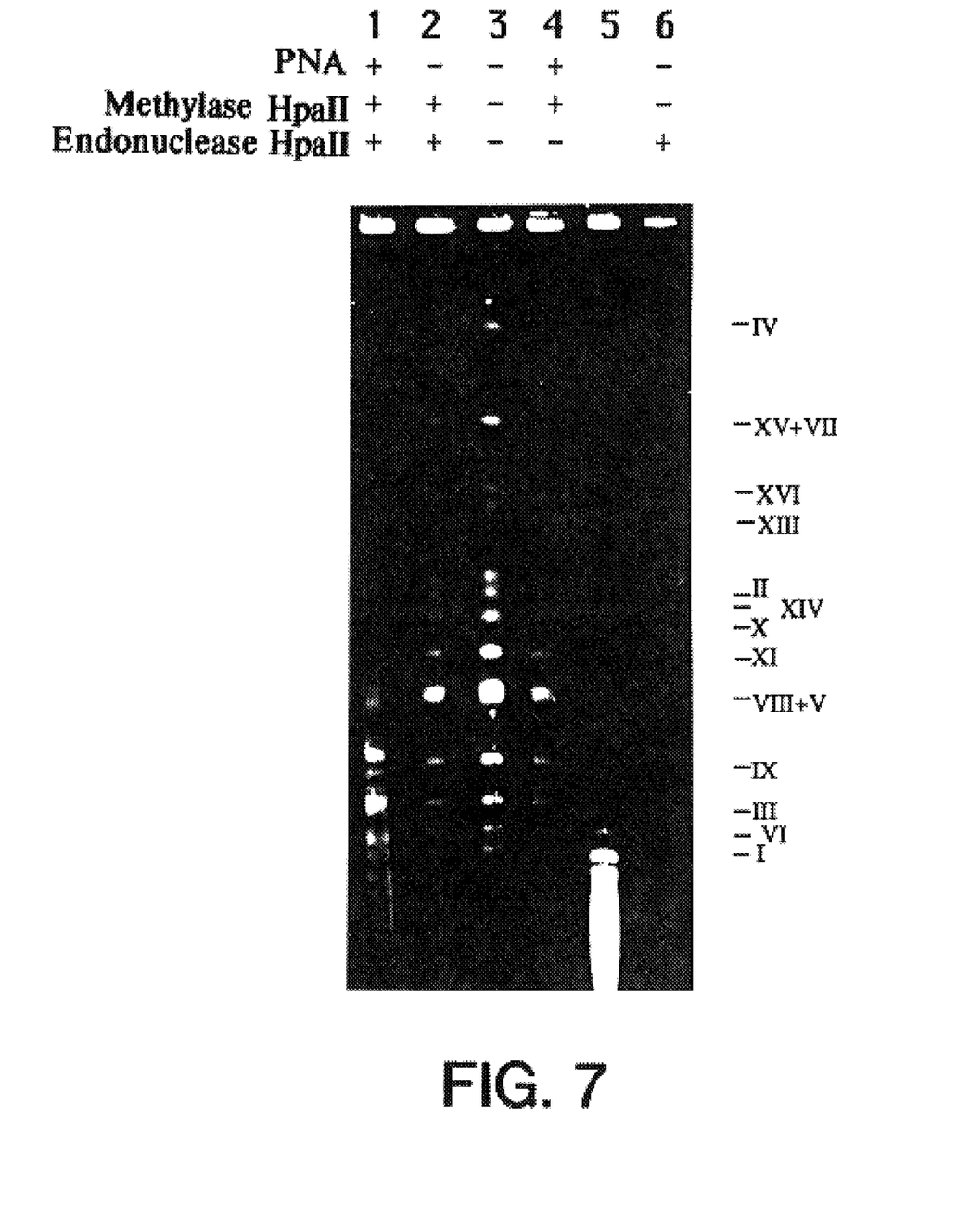
FIG. 7 Nucleic acid clamp alters cleavage specificity of Hpa II methylase/Sma I endonuclease treatment.

PFGE Separation of Yeast Genome Following Treatment with PNA669 and Hpa II Methylase and Endonuclease To determine the effectiveness of nucleic acid clamps on larger genomes, yeast target DNA was used in nucleic acid clamp modified digestion. Conditions used were the same as in example 2 except an agarose plug of 15 µl was used. The nucleic acid clamp, PNA-669 was applied at a concentration of 0.055 o.u. Results are shown in FIG. 7. Sma I and Hpa II digest, shown in lane 5 and 6 respectively, results in complete digestion of yeast DNA. Undigested DNA, lane 3, and DNA which underwent the procedure without PNA (lane 2) or without endonuclease (lane 4) are identical within the limits of this technique. Yeast genomic DNA treated with nucleic acid clamp, methylase, and endonuclease are digested into a small number of fragments (lane 1).

Other embodiments and uses of the invention will be apparent to those skilled in the art from consideration of the specification and practice of the invention disclosed herein. All U.S. Patents and other references cited herein are specifically incorporated by reference. The specification and examples should be considered exemplary only with the true scope and spirit of the invention indicated by the following claims.

We claim:

1. A method for sequence specific cleavage of a target nucleic acid comprising the steps of:

a) contacting a nucleic acid clamp to a target nucleic acid to form a triple helix, wherein said nucleic acid clamp comprises a first peptide nucleic acid (PNA) sequence and a second PNA sequence each containing one or more pseudocytosines, a bend region comprising a plurality of dioxaoctanoic acid residues connecting an end of said first PNA sequence to an end of said second PNA sequence, and a stabilizer comprising one or more positively charged residues covalently connected to a another end of a said first or second PNA sequences, said residues selected from a group consisting of lysine, arginine, histidine, and ornithine;

b) methylating said target nucleic acid to create methylated target nucleic acid;

c) separating said nucleic acid clamp from said methylated target nucleic acid; and d) digesting said methylated target nucleic acid with an endonuclease;

wherein said target nucleic acid is specifically cleaved.

2. The method of claim 1 wherein said target nucleic acid is methylated by a methylase selected from a group consisting of dam methylase, dcm methylase, EcoK methylase, CpG methylase, type I modification enzymes, type II modification enzymes and type III modification enzymes.

3. The method of claim 1 wherein said nucleic acid clamp first sequence contains between about 4 to about 15 residues.

4. The method of claim 1 wherein said nucleic acid clamp second sequence contains between about 4 to about 15 residues.

* * * * *

UNITED STATES PATENT AND TRADEMARK OFFICE
CERTIFICATE OF CORRECTION

PATENT NO : 6,004,750

DATED : December 21, 1999

INVENTOR(S) : Maxim D. FRANK-KAMENITSKII, et al.

It is certified that error appears in the above-identified patent and that said Letters Patent are hereby corrected as shown below:

Col. 1, line 5
  add --This invention was made with government support under Contract Nos GM52201 and GM54434 awarded by the National Institutes of Health. The government has certain rights in the invention. --

Signed and Sealed this

Twenty-fourth Day of April, 2001

Attest:

NICHOLAS P. GODICI

Attesting Officer

Acting Director of the United States Patent and Trademark Office

```
                         SEQUENCE LISTING

<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:  Synthetic

<400> SEQUENCE: 1
tccccttcga                                                            10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:  Synthetic

<400> SEQUENCE: 2
aggggaagct                                                            10
```